US010137032B2

(12) United States Patent
Williamson et al.

(10) Patent No.: US 10,137,032 B2
(45) Date of Patent: Nov. 27, 2018

(54) SLUSH GENERATION

(71) Applicant: 42 TECHNOLOGY LIMITED, St Ives, Cambridgeshire (GB)

(72) Inventors: Finbarr Charles Williamson, St Ives (GB); Roderick Andrew Haines, St Ives (GB); Simon Philip Jelley, St Ives (GB)

(73) Assignee: 42 TECHNOLOGY LIMITED, Cambridgeshire (GB)

( * ) Notice: Subject to any disclaimer, the term of this patent is extended or adjusted under 35 U.S.C. 154(b) by 200 days.

(21) Appl. No.: 14/771,433

(22) PCT Filed: Mar. 6, 2014

(86) PCT No.: PCT/GB2014/050669
§ 371 (c)(1),
(2) Date: Aug. 28, 2015

(87) PCT Pub. No.: WO2014/135886
PCT Pub. Date: Sep. 12, 2014

(65) Prior Publication Data
US 2016/0030235 A1    Feb. 4, 2016

(30) Foreign Application Priority Data

Mar. 7, 2013   (GB) .................... 1304131.4

(51) Int. Cl.
*F25C 1/22*     (2018.01)
*A61F 7/00*     (2006.01)
(Continued)

(52) U.S. Cl.
CPC .............. *A61F 7/0085* (2013.01); *A61F 7/10* (2013.01); *F25C 1/00* (2013.01); *A61F 2007/0056* (2013.01); *F25C 2301/002* (2013.01)

(58) Field of Classification Search
CPC .... A61F 7/0085; F25C 1/00; F25C 2301/002; B67D 1/0857; B67D 3/009; B67D 1/0054; B67D 1/0859; B67D 1/0864; A23G 9/045
See application file for complete search history.

(56) References Cited

U.S. PATENT DOCUMENTS 3,823,571 A     7/1974   Smith et al.
5,974,824 A *  11/1999   Galockin ............. B67D 1/0864
                                              222/146.6
(Continued)

FOREIGN PATENT DOCUMENTS

EP       1738652 A2      1/2007
EP       1980156 A1     10/2008
(Continued)

OTHER PUBLICATIONS

Search Report for United Kingdom Application No. GB1403985.3 dated Sep. 2, 2014, 2 pages.
(Continued)

*Primary Examiner* — Elizabeth Martin
(74) *Attorney, Agent, or Firm* — Withrow & Terranova, P.L.L.C.; Vincent K. Gustafson

(57) ABSTRACT

Apparatus for generating, at a target ice/liquid ratio with a corresponding target temperature, a slush comprising frozen and non-frozen liquid comprises a flow path for recirculation of liquid therethrough, the flow path comprising a heat exchanger having a coolant inlet and a coolant outlet, the heat exchanger being configured for flow therethrough of coolant at a temperature below the target temperature, the apparatus being configured to vary the rate of coolant flow through the heat exchanger between a first rate and a second rate that is lower than the first rate.

23 Claims, 9 Drawing Sheets

(51) Int. Cl.
*F25C 1/00* (2006.01)
*A61F 7/10* (2006.01)

(56) References Cited

U.S. PATENT DOCUMENTS

| | | | |
|---|---|---|---|
| 7,874,167 B2 | 1/2011 | Kammer et al. | |
| 2001/0041210 A1* | 11/2001 | Kauffeld | A23G 9/045 426/590 |
| 2008/0149655 A1 | 6/2008 | Gist et al. | |
| 2008/0289357 A1* | 11/2008 | Skobel | A23G 9/045 62/386 |
| 2009/0314011 A1* | 12/2009 | Simmons | B67D 1/0054 62/66 |
| 2010/0212336 A1* | 8/2010 | Chapman | F25C 5/002 62/99 |
| 2011/0088413 A1* | 4/2011 | Lampe | C09K 5/066 62/68 |

FOREIGN PATENT DOCUMENTS

| | | | |
|---|---|---|---|
| EP | 2446750 | A1 | 5/2012 |
| GB | 2452918 | A | 3/2009 |
| JP | H05-332649 | A | 12/1993 |
| JP | 2005-344995 | A | 12/2005 |
| WO | 00/33665 | A1 | 6/2000 |
| WO | 2004088220 | A1 | 10/2004 |
| WO | 2009037446 | A2 | 3/2009 |
| WO | 2009117586 | A2 | 9/2009 |
| WO | 2011051707 | A2 | 5/2011 |

OTHER PUBLICATIONS

International Search Report (Form PCT/ISA/210) and Written Opinion (Form PCT/ISA/237) for International Patent Application No. PCT/GB2014/050669 dated Jun. 2, 2014, 9 pages.

Communication pursuant to Article 94(3) EPC for European Patent Application No. 14714770.6 dated May 26, 2017, 4 pages.

Notification of Reasons for Refusal for Japanese Patent Application No. 2015-0560776 dated Mar. 12, 2018, 4 pages.

\* cited by examiner

SLUSH GENERATION

STATEMENT OF RELATED APPLICATIONS

This application is a 35 U.S.C. § 371 national phase filing of International Application No. PCT/GB2014/050669 filed on Mar. 6, 2014, and further claims priority to United Kingdom Patent Application No. 1304131.4 filed on Mar. 7, 2013, with the disclosures of the foregoing applications hereby being incorporated by reference herein in their respective entireties.

TECHNICAL FIELD

The present invention relates to generating a slush comprising frozen and non-frozen liquid, in particular but not exclusively to generating a slush beverage.

BACKGROUND ART

Slush generation machines that provide a partially frozen liquid are well known. Such machines are often used to create a semi-frozen slush that can be used when a high thermal capacity fluid coolant is needed to provide either a high rate of cooling or consistent cooling for long periods. Typically, the slush is formed from water with a freeze point suppressant—common examples of which include sugars, salts, alcohols and glycols—which decreases the freeze temperature and stops ice crystals joining together and blocking the machine.

Slush machines are used in the medical industry when saline slush is used to cool tissue to reduce metabolic rate to reduce damage during surgical procedures and in sports therapy to accelerate healing of injuries. Of the slush machines used to create slush for surgical procedures many create the small ice crystals needed to make the semi-liquid slush either by freezing the working fluid on a refrigerated surface and then removing it using a mechanical scraper or by mechanically flexing the surface. Such systems are generally expensive, requiring large geared motors to drive the scrapers or surface flexing mechanisms. The key requirement of a slush fluid for use in medical procedures, particularly when the slush is used internally, is that the fluid is sterile to prevent infection. Scraped surface slush machines are unsuited to this application as the freezer system is fundamentally expensive and so must be a reusable component that must be regularly sterilised. US007874167B2 describes a machine for creating slush for surgical use. Other applications of slush include food processing and cold storage for air conditioning.

Slush generation machines that provide a partially frozen liquid beverage are also well known. Unlike drinks containing water ice cubes, they provide beverages in which the beverage itself is frozen and used to maintain a low drink temperature throughout consumption. This has the advantage of maintaining the concentration of the flavouring ingredients of the beverage and not 'watering down' the drink. In addition, the texture of the ice crystals in the drink can provide a desirable 'mouth feel' and enhanced experience for the consumer. Two types of system for the production of slush beverages are known.

In the first type of system, liquid beverage dwells in a refrigerated chamber and turns to ice on the refrigerated surface of the chamber. This ice is dislodged by means of a scraper to mix with the liquid and form a slush. Such scraped surface freezer systems are disclosed e.g. in WO2009/037446, WO2009/060169, EP1738652, WO2004/088220, U.S. Pat. No. 3,823,571 and EP2446750. These systems tend to be very expensive due to the large geared motors needed to drive the scrapers. In addition, particularly when pressurised, these systems are unreliable as the rotating seals needed to transmit the mechanical power are prone to failure. Other drawbacks to these systems include high energy input due to the use of vapour compression refrigeration systems to directly cool the freezer surfaces. To achieve sufficient cooling power to provide the required throughput of slush beverages the refrigeration plants must be large, low temperature, systems giving low coefficients of performance and high energy input. The cost of product wastage when the systems are cleaned, particularly when the beverage is expensive such as with alcoholic drinks, can also be a problem. With scraped surface ice generators the typical holding volume is several liters, all of which will be discarded when the system is cleaned.

In the second type of system, liquid beverage does not dwell but instead recirculates through at least one long coil that is suspended in a glycol cooling medium. Such systems are disclosed in US2001/0041210 and WO2011/051707. Ice forms in the liquid, resulting in a slush, the temperature of the cooling medium being chosen to achieve the desired ice/liquid ratio in the slush—WO2011/051707 discloses a temperature of −5.6° C. corresponding to an estimated 20% ice/liquid ratio and a temperature of −6.4° C. corresponding to 24% ice/liquid ratio. This temperature must be limited so as to avoid complete freezing of the slush in the conduit when throughput is low and little or no unfrozen liquid is entering to replace dispensed partially frozen liquid. To achieve the freeze rate necessary for when the throughput is higher, the length of the conduit must be increased to around 72 m in length, making the apparatus as a whole less compact. In addition, the system uses one or more variable speed pumps for the beverage and an integrated refrigerating system with a glycol bath. As a result, it is inherently large, complicated and expensive.

DISCLOSURE OF INVENTION

According to the present invention, there is provided apparatus for generating, at a target ice/liquid ratio with a corresponding target temperature, a slush comprising frozen and non-frozen liquid, the apparatus comprising a flow path configured for recirculation of liquid therethrough; wherein the flow path comprises a heat exchanger having a coolant inlet and a coolant outlet, the heat exchanger being configured for flow therethrough of coolant at a temperature below the target temperature, the apparatus being configured to vary the rate of coolant flow through the heat exchanger between a first rate and a second, lower rate.

The invention is based on the recognition that the coolant temperature in a recirculating type of system for generating slush having a target ice/liquid ratio can be lower than that used in systems of the kind discussed above as long as the cooling of the liquid by that lower-temperature coolant can be reduced, e.g. once the target ice/liquid ratio is achieved. In addition, varying the rate of coolant flow enables the rate of heat transfer out of the liquid (in units of energy per second, Watts) to be varied, which in turn enables the fraction of frozen liquid in the slush to be controlled substantially independently of the rate at which slush is fed through the apparatus.

The apparatus may be configured such that the first rate of coolant flow produces a net increase in the fraction of frozen liquid in the total liquid contained in the flow path.

Thus when slush is dispensed from the apparatus, to be replaced by fresh, unfrozen liquid, the heat exchanger can be operated at the first, higher rate of heat transfer so as to partially freeze that unfrozen liquid. However, once the desired fraction of frozen liquid in the slush has been reached, the heat exchanger can be operated at the second, lower rate, so as to avoid reaching a higher fraction of frozen liquid than required. In order to maintain a required fraction of frozen liquid the heat exchanger can either vary the heat transfer rate until the net rate of heat transfer from the system is zero, or it can switch between heat transfer rates that achieve net positive and net negative heat transfer rates such that over time the net heat transfer is zero and the desired fraction of frozen liquid within the system is maintained.

Specifically, the apparatus may be configured such that the second rate of coolant flow produces a net decrease in the fraction of frozen liquid in the flow path. The apparatus may be configured such that the second rate of coolant flow produces substantially no change in the fraction of frozen liquid in the flow path.

The apparatus may be configured to maintain a liquid flow rate through the flow path of at least 1 liter per minute. The inventors have established that operation below this level may be unreliable when ice first nucleates.

The coolant may be a liquid.

The apparatus may comprise a coolant pressure generator configured to feed coolant from the coolant inlet to the coolant outlet of the heat exchanger.

The apparatus may comprise a sensor for sensing the fraction of frozen liquid in the generated slush, the device being configured to vary the rate of coolant flow through the heat exchanger in dependence on the output from the sensor. Where the apparatus comprises an electrically-driven pump for recirculating liquid around the conduit loop, the sensor may be configured to generate an output in dependence on the electrical supply to the pump, in particular the electrical current drawn by the pump.

The apparatus may comprise a flow restrictor for restricting coolant flow through the heat exchanger.

The apparatus may comprise a flow diverter for diverting coolant flow away from the heat exchanger.

The apparatus may comprise a pump to vary the rate of coolant flow through the heat exchanger.

The apparatus may comprise a further flow path configured to re-circulate coolant from the coolant outlet back to the coolant inlet.

The apparatus may comprise a housing and be configured for releasable connection of the coolant inlet to a separate coolant supply that is outside of the housing, in which case the further flow path is configured to re-circulate coolant via that separate coolant supply. The use of such a separate 'stand alone' chiller unit allows the apparatus itself to be less complex and lower cost.

The flow path configured for recirculation of liquid therethrough may be defined by a conduit loop.

The conduit loop may consist of tubing having a medium density polyethylene (MDPE) or nylon bore. The tubing may have a wall thickness less than about 1.4 mm.

According to the present invention, there is also provided a beverage dispenser comprising apparatus for generating a slush as set out above and a dispensing outlet in fluid communication with the flow path.

According to the present invention, there is also provided cryotherapy apparatus comprising apparatus for generating a slush as set out above and a further heat exchanger for throughflow of slush from the flow path, the further heat exchanger being configured for application to a patient.

According to the present invention, there is also provided apparatus for generating a slush as set out above and in which all parts wetted by the liquid are configured to be disposable. The flow path may be sealed except for a dispensing outlet, thereby improving the sterility of the slush.

The heat exchanger may comprise a coolant conduit that is releasably attached for heat exchange to the conduit loop, thereby allowing the conduit loop to be removed from the apparatus and disposed of, to be replaced by a fresh conduit loop. The conduit loop may include a liquid reservoir, which may have flexible walls.

According to the present invention, there is also provided a method of generating, at a target ice/liquid ratio with a corresponding target temperature, a slush comprising frozen and non-frozen liquid, the method comprising the steps of:

providing a flow path for recirculation of liquid therethrough, the flow path comprising a heat exchanger having a coolant inlet and a coolant outlet;

recirculating liquid through the flow path;

feeding coolant through the heat exchanger at a temperature below the target temperature; and varying the rate of coolant flow through the heat exchanger between a first rate and a second, lower rate.

The method aspects of the invention can be particularlised using features of the apparatus described above.

BRIEF DESCRIPTION OF DRAWINGS

An embodiment of the invention will now be described by way of example with reference to the accompanying drawings, in which.

DETAILED DESCRIPTION OF SPECIFIC EMBODIMENTS

Figure 1:
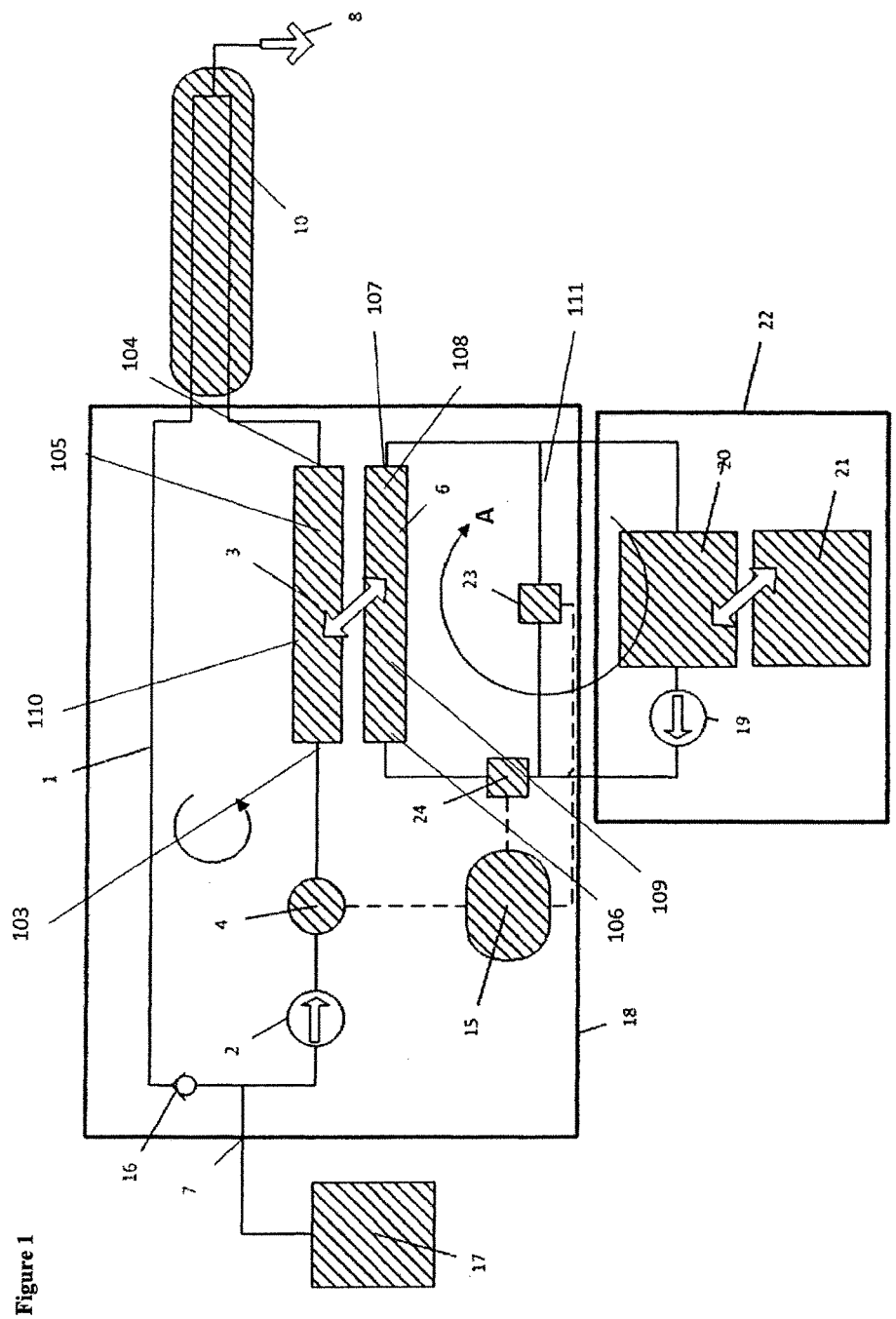
FIG. 1 is a diagrammatic view of a first embodiment of the invention.

Referring to FIG. 1, apparatus for generating a slush comprising frozen and non-frozen liquid comprises a freeze conduit 3 for liquid 110, the conduit having an inlet 103 and an outlet 104 defining a volume 105 therebetween. In the example shown, the liquid is a beverage comprising water and other flavouring ingredients, optionally including alcohol and/or dissolved carbon dioxide, in particular water-based beverages containing alcohol at a concentration less than 10% such as beer, lager and cider. Volume 105 is chosen to be greater than the desired dispense volume (discussed below), so as to avoid unfrozen beverage being dispensed.

A liquid pressure generator, namely pump 2, feeds liquid through the volume 105 from the inlet 103 to the outlet 104 where it is then re-circulated back to the inlet 103 via conduit 1, conduit 1 and freeze conduit 3 together defining a conduit loop for recirculation of liquid. Slush can be dispensed from the loop, e.g. into a glass or beaker, from dispensing outlet 8, the loop being replenished via conduit loop inlet 7 from a reservoir 17.

In the embodiment shown, pump 2 is a fixed displacement diaphragm pump, capable of a maximum pressure of 9 bar and a maximum flow rate of 3 liters per minute, and located upstream of the freeze conduit so as to be able to drive fluid through the freeze conduit at higher pressure, thereby improving reliability.

To enable the slush beverage to be dispensed remotely at a convenient location remote from the slush generating section of the slush machine in a housing 18, an insulated slush recirculation umbilical 10 is added between the slush machine 18 and the dispensing outlet 8. This component typically consists of two lengths of standard beverage tubing encased in thermal insulation, the dispensing outlet being a standard bar font. To ensure the slush beverage is dispensed from the freeze conduit a non-return valve 16 is added to the return leg of the re-circulated loop.

Reservoir 17 may be pressurised so as to provide motive force to overcome the pressure head losses in the pipework supplying the beverage to the slush machine at the desired dispense flow rate. When a beverage is carbonated, it may be desirable to supply the beverage at a higher pressure, one which maintains the desired carbonation level of the beverage within the pressure vessel at the storage temperature: in this case it may be necessary to include a fluid restriction (not shown) in either the fluid input line 7 or the dispensing outlet 8 to achieve the desired dispense flow rate. Alternatively, if the reservoir is not pressurised, or insufficiently pressurised for driving the dispense of the liquid, for example to avoid over-carbonation or if the reservoir is at a low height relative to the dispense point, a boost pump (not shown) may be employed to give the motive force to achieve the required dispense rate.

An additional chiller unit (not shown) may also be provided to reduce the temperature of the liquid from the reservoir prior to entry into the conduit loop: to reduce the cooling energy required to freeze the beverage to the desired ice fraction, the beverage is supplied to the slush machine at a temperature as close to its freeze point as possible. In the embodiment described here acceptable performance was achieved when the beverage was supplied at 3° C. from the pressurised vessel with the freeze point being approximately −3° C. giving a 6° C. temperature drop before the beverage begins to freeze.

As indicated by the double-headed arrow, the freeze conduit 3 forms one half of a heat exchanger 6 with a cooling conduit 108 having an inlet 106 and an outlet 107 and containing a body of liquid glycol coolant 109 therebetween. Heat exchanger 6 is connected to a coolant loop that, as indicated by arrow A, circulates the liquid coolant from the inlet 106 to the outlet 107 to a coolant refrigeration unit 22 and then back to the inlet 106.

The coolant is provided to the inlet of the cooling conduit at a temperature below the freeze point of the liquid; thus, when the coolant flows within the cooling conduit thermal heat transfer occurs from the liquid to the coolant. As the net thermal heat transfer to the coolant is positive the temperature of the coolant downstream of the entrance to the cooling conduit is greater than the temperature of the coolant supplied by the coolant source at the entrance.

In the embodiment shown, coolant refrigeration unit 22 is a separate, standard glycol chiller commonly used in bar environments which includes a vapour compression refrigeration system 21 that is used to cool a reservoir of coolant 20. Pump 19 is integrated into the chiller unit and provides the motive force to re-circulate the coolant. The refrigeration capacity of the chiller used in this embodiment is 1.3 kW at −6° C. with the liquid pump capable of a maximum flow of 13 liters per minute or maximum head lift of 16 meters. The use of such a separate 'stand alone' chiller unit allows the slush generating apparatus itself to be less complex and lower cost.

The rate of flow of liquid coolant through the cooling conduit 108 can be varied, thereby varying the rate of heat transfer out of the liquid in the volume 105 of the freeze conduit 3. By varying the flow rate of fresh coolant into the cooling conduit a net increase or decrease in the average temperature of the coolant within the cooling conduit is effected: this changes the overall thermal heat transfer rate from the working fluid to the coolant and hence the freeze rate in the working fluid flowing within the freeze conduit.

In the example shown, flow through the cooling conduit is controlled by a 2/2 way normally closed solenoid valve 24 with a large 20 mm orifice giving a low restriction to flow when open. In this simple embodiment the lower rate of heat transfer is achieved by shutting off the coolant fluid flow rate to substantially zero and the apparatus uses on-off pulses to control the ice fraction. An alternative option to achieve finer control is to use a variable restriction valve such as a flow regulator or butterfly valve to vary the flow substantially continuously between full flow and zero flow, although the inventors have found that the time constant of the coolant temperature change with flow rate smooths out the on-off pulses, and acceptable control has been achieved without the additional cost and complexity of a variable restriction. Another alternative to a single large orifice 2/2 valve is the use of a plurality of smaller orifice 2/2 valves in parallel; as smaller orifice valves are more common, this option may prove a cheaper design as well as enabling some variable flow control should this later be found to be beneficial. To prevent 'dead heading' of the coolant pump an additional coolant bypass loop 111 is provided for diverting coolant flow away from the cooling conduit, flow through this loop being controlled as required by a 2/2 way normally open solenoid valve 23. Thus the coolant flow can be diverted in either of two directions; through the cooling conduit or around the cooling conduit through the coolant bypass loop. Without extra cost or complexity these two coolant control valves enable a third state, with both valves open, where the bypass loop will take a proportion of the flow resulting in a reduced but non-zero flow through the cooling conduit. Alternative methods for controlling the coolant bypass and avoiding 'dead heading' include using a pressure relief valve on the bypass that only opens when the pressure rises due to no flow in the cooling conduit, or using a 3/2 valve to replace both 2/2 coolant valves 23, 24 shown in FIG. 1 such that the 3/2 valve diverts coolant flow either through the cooling conduit or around the coolant bypass loop.

As indicated by dashed lines in FIG. 1, valves 23, 24 are controlled by a controller 15 in dependence on a sensor 4 to sense the fraction of frozen liquid in the generated slush. In the embodiment shown, the sensor is provided in the conduit loop 1 immediately upstream of the conduit inlet 103 so as to be able to quickly sense incoming unfrozen fluid during dispense to quickly increase cooling power to reduce ice recovery time. Such sensors operate on various principles: for example, it is well known that an increase in the suspended solid particle content (ice/liquid ratio) of a slush or slurry acts to increase its apparent viscosity. A sensor may make use of this phenomenon, detecting the ice/liquid ratio in the re-circulated beverage using a pressure sensor placed between the pump and the freeze conduit. An increase in viscosity of the slush flowing in the recirculated loop causes an increase in the pressure at the exit of the pump. This is detected by the pressure sensor so providing an indirect method of measuring the ice/liquid ratio of the slush beverage in the re-circulated loop. To avoid pressure fluctuations caused by dispensing the liquid affecting the inferred ice/liquid ratio, the differential pressure across the ice generator can be measured by comparing pressure before and after the freeze conduit. Depending on pump type, a measurable increase in electrical current may be seen with increasing ice/liquid ratio due to the pressure across the pump increasing, where this current change may enable the sensing to be performed without a separate dedicated sensor. The inventors also envisage an alternative controller where a mechanical pressure sensor such as a piston or diaphragm between the recirculation loop either side of the freeze conduit acts directly to actuate a valve on the coolant circuit, thereby controlling the ice/liquid ratio. In such an arrangement the target ice/liquid ratio may be set by biasing the sensor with a force that corresponds to the pressure at the required ice/liquid ratio by means of a spring, for instance. Other known ways to sense the ice/liquid ratio may be based on the density or turbidity of the slush. Turbidity sensing may be preferred where a quick response to changes in ice/liquid ratio is required, while pressure sensing enables the average ice/liquid ratio in the conduit to be detected, lessening sensitivity to uneven ice/liquid ratios within the working fluid loop.

In the embodiment shown, the controller 15 can vary the heat transfer out of the liquid in volume 105 between different rates by controlling the flow of liquid coolant through the cooling conduit in dependence on the output from the sensor 4. In this embodiment, the controller is a proportional integral derivative controller. The embodiment shown has two main operational usage states; the first, its idle state, when no dispense is occurring, and the second state, ice/liquid ratio recovery, occurring during and just after dispense has occurred.

In the idle state, the machine is only required to overcome the base energy gains in the system from the fluid moving means, through the insulation, and from the other components to maintain the ice/liquid ratio of the working fluid in the re-circulated loop to the pre-set level desired by the operator so that it is always ready for dispense. Indeed, the apparatus may be configured such that the second rate of heat transfer produces a net decrease in the ratio of frozen liquid in the total liquid contained in the apparatus. In this usage state the cooling power required is low. The ice/liquid ratio set point is maintained by occasionally pulsing on the coolant flow through the cooling conduit as required to maintain the ice/liquid ratio at the pre-set level, where the net increase in ice/liquid ratio from the pulse balances the net decrease caused by the base line of the second rate of heat transfer when the coolant is diverted from the cooling conduit.

When dispense occurs, the volume of semi frozen working fluid dispensed is replaced with unfrozen working fluid from the reservoir. This results in a rapid reduction in the solid fraction of the fluid within the re-circulated loop that is immediately sensed by the sensor 4, causing the control system to increase the rate of heat transfer out of the freeze conduit so as to produce a net increase in the fraction of frozen liquid in the total liquid contained in the apparatus and regain the required pre-set solid fraction target level.

In this state the cooling power required is high as it is desirable to regain the solid fraction level as quickly as possible so that the machine can dispense the working fluid with consistent solid fraction. Here the coolant flow control means will be operated by the control system to stay in the high freeze rate state until such a time as the solid fraction in the re-circulated loop is regained substantially to the pre-set level, at which time the heat exchanger can be operated at a lower rate. The controller may anticipate the ice fraction recovering, for example by the derivative term in the PID control algorithm, switching to the lower rate of cooling shortly before reaching the ice fraction set point so as to avoid overshooting the pre-set level.

Figure 8:
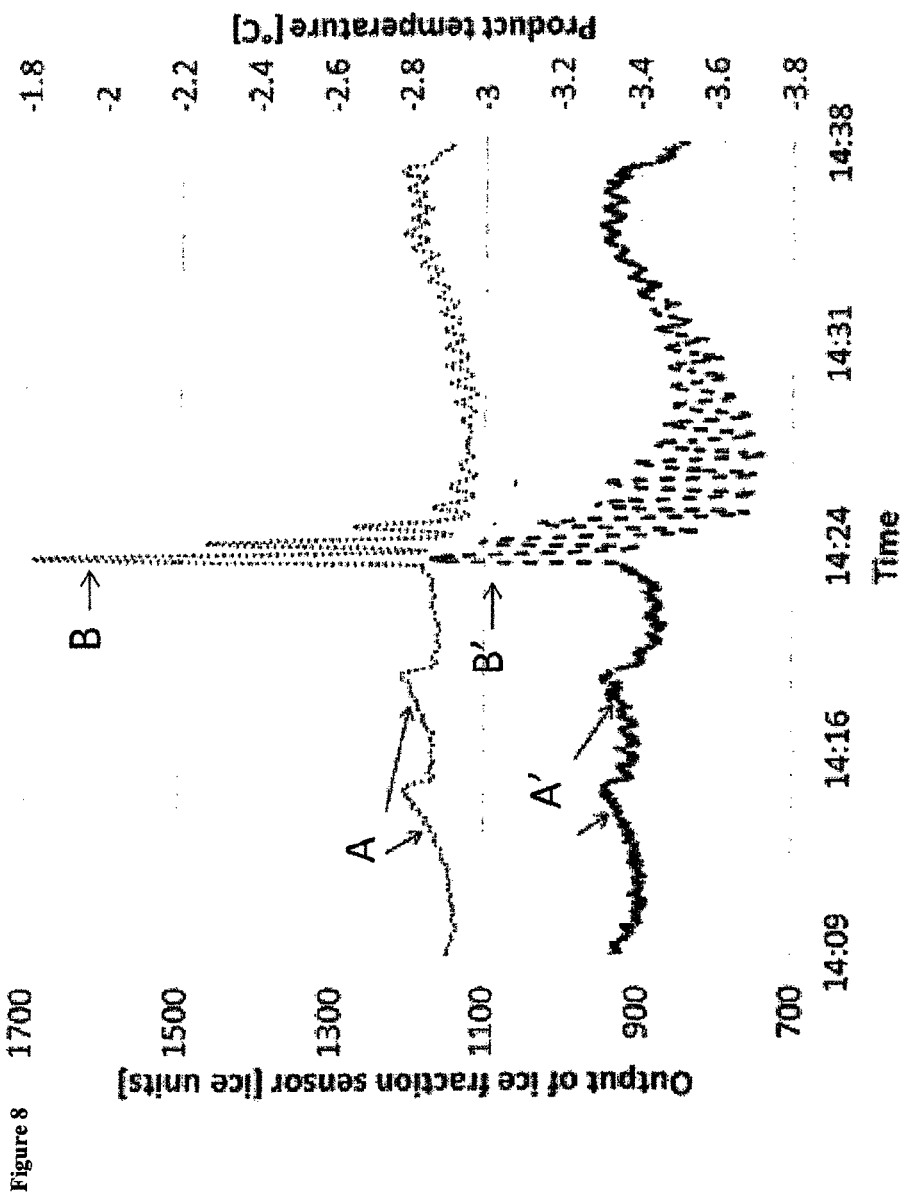
FIG. 8 illustrates a typical variation over time in product temperature and the output of an ice fraction sensor.

FIG. 8 illustrates a typical variation over time in product temperature (in degrees Celsius) and the output of an ice fraction sensor in ice units, the latter being inversely proportional to the actual ice/liquid ratio of the product. Product temperature is indicated by the bold dashed line while sensor output is indicated by the dotted line. In the example shown, the target ice fraction is around 1100 ice units, corresponding to a target temperature of around −3.7° C. The dispensing of small amounts of product out of the flow path results in corresponding small decreases in ice fraction and increases in product temperature as indicated at A and A' respectively. The dispensing of larger amounts of product result in correspondingly larger changes in ice fraction and product temperature as indicated at B and B'. It will be appreciated that different liquids—e.g. different beverages with different concentrations of alcohol and sugar—may exhibit different changes in temperature for similar changes in ice fraction.

Figure 9:
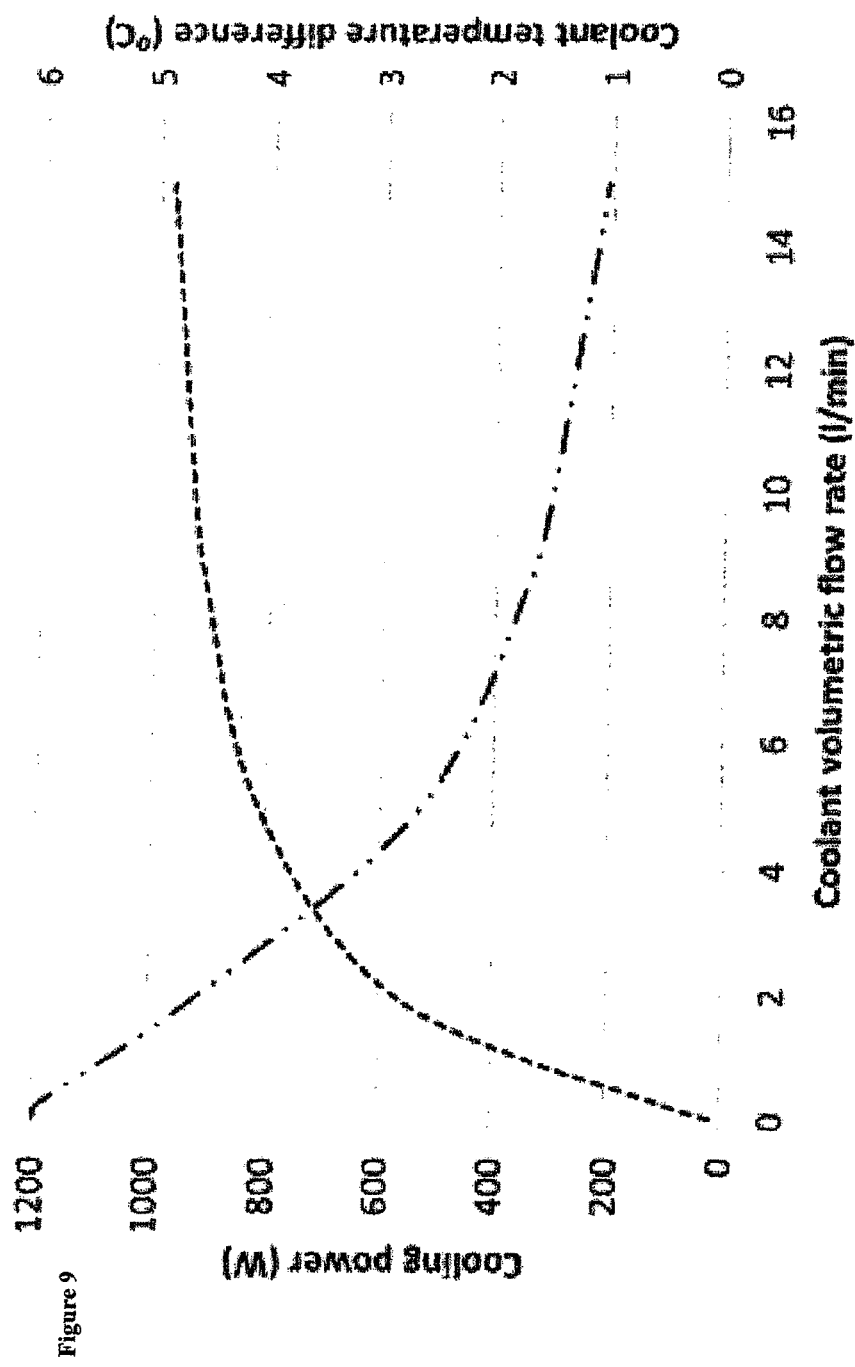
FIG. 9 illustrates the variation in cooling power with coolant flow rate and the corresponding increase in temperature of the coolant from inlet to outlet.

Particularly, the coolant flow is variable to at least two flow rates; a first flow rate that results in a high freeze rate, greater than the melt rate in the rest of the system, and a second flow rate at a level which, if maintained, results in a low freeze rate, less than the melt rate in the rest of the system. Thus, the first coolant flow rate causes a net increase in the solid to liquid fraction of the working fluid within the re-circulated loop and the second coolant flow rate causes a net reduction in the solid to liquid fraction of the working fluid within the re-circulated loop. By operating the coolant flow control means in response to the output of the solid to liquid fraction sensing means the solid to liquid fraction of the working fluid within the re-circulated loop is accurately controlled to any level required. FIG. 9 illustrates the variation in cooling power of the heat exchanger (dashed line) with coolant flow rate through the heat exchanger and the corresponding increase in temperature of the coolant from inlet to outlet of the heat exchanger (dot-dash line). For example, where six pints are dispensed over 20 minutes with a 50 W heat gain, the required average flow rate of coolant may be around 0.46 liters/minute. This may be achieved by a substantially constant flow or by a series of flow pulses, e.g. a 10 second pulse of 2.76 liters/minute once per minute for twenty minutes.

Where it is advantageous to recover more quickly after dispense, the apparatus may further comprise a means of detecting dispense quickly, such that the controller can pre-empt the arrival of unfrozen liquid at the ice fraction sensor. This will allow more time for cold coolant to flow into the cooling conduit, enabling a faster recovery to the required ice fraction. There are a number of simple methods for detecting dispense occurring, such as a switch on the tap, a flow switch on the liquid input line or a pressure sensor to detect the drop in pressure as the tap is opened.

The coolant is provided at a temperature below the target freeze temperature to achieve a target ice/liquid ratio. In practice, it has been found that a temperature difference between the target beverage freeze temperature and the coolant input temperature of between 2° C. and 9° C., particularly 6° C., produces acceptable performance. It has also been found that a liquid flow rate through the freeze conduit of at least 1 liter per minute is desirable to achieve reliable performance when the ice first nucleates.

As an example, where a single drink of 1 pint (568 mL) is dispensed every 30 seconds with a fluid inlet temperature of 3° C., a target freeze temperature of −3° C. to achieve an ice fraction of 8%, the required total average cooling power is 0.98 kW. It has been determined by the inventors that to maintain drink consistency the system should contain at least one dispense volume. Thus with the preferred concentric ice generation conduit configuration with an internal diameter of 7.4 mm approximately 13.2 m of conduit contains the required volume of beverage to maintain drink consistency. Such a length of 1 mm walled MDPE tube can achieve the 0.98 kW heat flow out of the working fluid with a coolant input temperature in the preferred range given. In addition, to be able to maintain the desired throughput a glycol chiller with a cooling power of greater than 0.98 kW is needed.

In addition to the main mode of maintaining the ice fraction, and the optional mode of responding to a detected dispense before the ice fraction has changed (if such a mode and the additional dispense detection means are provided), the system shown in FIG. 1 has a third operational mode whereby it keeps the working fluid cool without generating ice. The requirement for dispensing may not be present overnight, so to minimise power consumption and to prevent Ostwald ripening, which tends to occur if the system is left for extended periods without dispensing, the system will not maintain the ice fraction, and will allow the slush to melt. It may be advantageous however to prevent the working fluid from warming up to ambient temperature, for example beverages need to be kept cool to prevent loss of freshness. The simplest method is to occasionally pulse on the coolant flow, based on dead reckoning control to maintain the working fluid temperature within acceptable limits. However, due to the possible range of conditions this approach will require keeping the working fluid colder than necessary to ensure the temperature remains in the acceptable range, so it may be beneficial to provide a working fluid temperature sensor to enable a more energy efficient overnight standby mode. Recirculation of the working fluid between coolant pulses may not be required, allowing a further reduction in energy usage.

Figure 2:
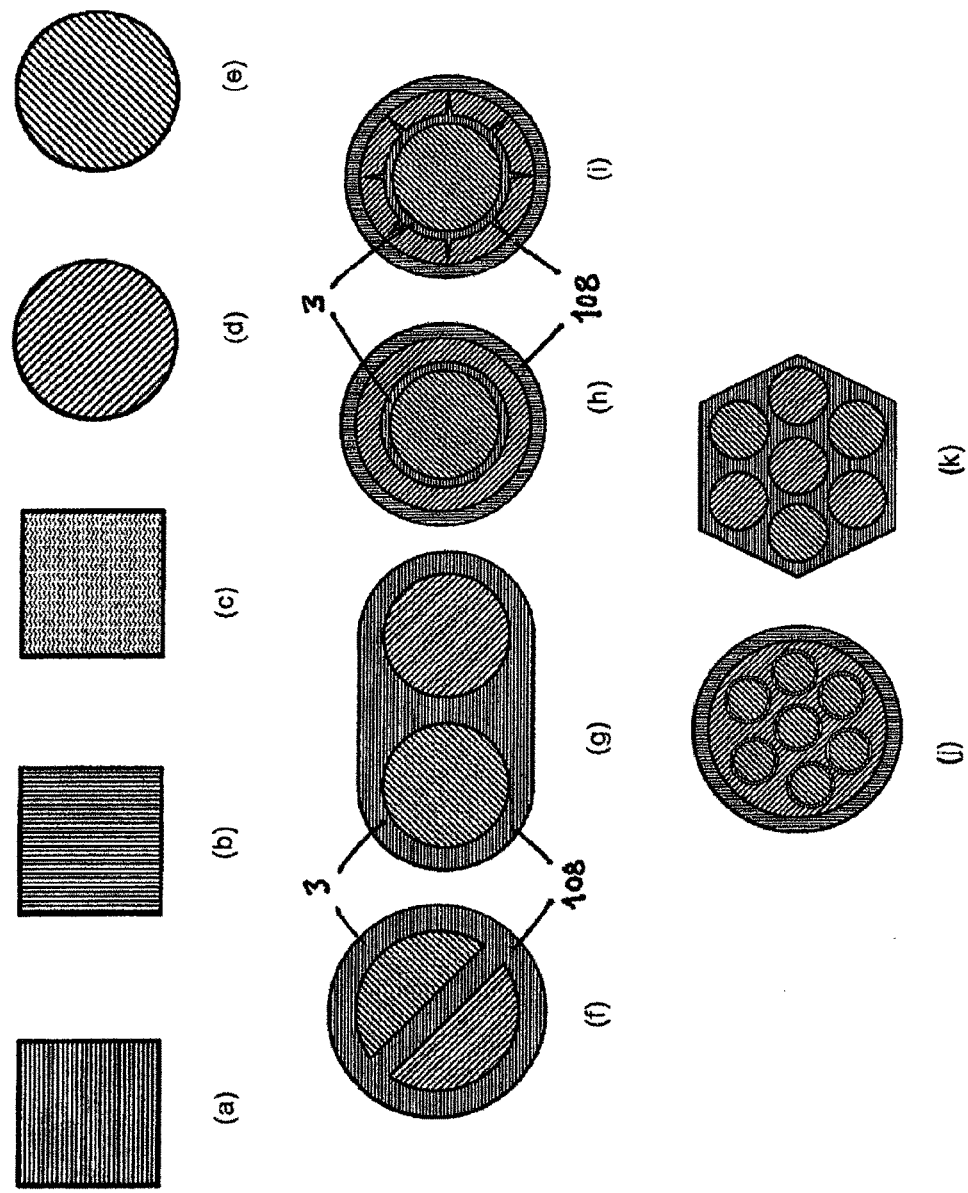
FIGS. 2(f) to (k) and 3 (a) to (e) are cross-sectional views through various embodiments of liquid and coolant fluid conduit.

FIG. 2 illustrates, in cross-section, various arrangements of freeze conduit 3 and coolant conduit 108 configured for heat transfer, with FIGS. 2(a) to (e) serving as a key for the different types of cross hatching used in the subsequent figures, viz:

(a)—material suitable for the freeze conduit;
(b)—material of construction is not important;
(c)—material with high thermal conductivity such as aluminium or copper;
(d)—coolant flow
(e)—liquid flow FIGS. 2(f) and (g) show examples of a parallel arrangement where the freeze conduit 3 and the cooling conduit 108 are made as a single piece. This arrangement gives the advantage of easy and cheap manufacture of the whole assembly as these cross sections could be easily extruded. However, as the main cross section must be made from a relatively low conductivity material and the proportion of the flow perimeter in close proximity for heat transfer is relatively small, this configuration may not be suitable where high cooling power is needed.

Referring to the embodiment of FIG. 2(h), a smaller freeze conduit 3 sits within the bore of a larger cooling conduit 108, the coolant 109 being in intimate contact with the exterior of the freeze conduit. Such a concentric arrangement allows the material of the freeze conduit 3 to be thin—in the case of medium density polyethylene (MDPE) tubing, a wall thickness of less than about 1.4 mm—reducing the thermal resistance between the coolant and the working fluid. This has the advantage of requiring smaller temperature difference between the coolant and the working fluid to generate a given heat flux. This enables the system that provides the coolant to be more energy efficient. In the example shown, the freeze conduit 3 consists of a length of standard beverage tubing of medium density polythene (MDPE) construction having an outer diameter of ⅜ inch and an internal diameter of 7 mm. Alternative suitable tubing materials—particularly for the bore of the tubing—include nylon, polytetrafluoroethylene (PTFE), fluorinated ethylene propylene (FEP), polypropylene (PP) and polyvinylchloride (PVC). The cooling conduit 6 consists of a length of 1 inch bore PVC tubing with fittings at both ends to admit both the smaller freeze conduit and the coolant input and output. To conserve space the freeze and coolant conduit assembly is coiled and, to reduce energy gains, is insulated. FIG. 2(i) shows the addition of radial spacers to ensure concentricity and even coolant flow around the freeze conduit; these spacers may be provided occasionally along the conduit length, or continuously and may be a separate part, a feature of either conduit wall or extruded as one piece with both conduit walls.

FIGS. 2 (j) and (k) show some examples of multiple flow paths alongside each other for both the coolant and the working fluid. These flowpaths may be connected in series or parallel, depending on whether tendency to block or restriction of flow is found to be the limiting factor. These arrangements allow an increase in contact area of the working fluid to the freeze conduit walls without increasing the overall length of the cooling conduit. This arrangement may be desirable in a high power slush machine to make the ice generator more compact. FIG. 2(k) shows the arrangement applied to the principle shown in FIGS. 2(f) and (g) giving a combination of the benefits of low cost manufacture and increased energy transfer.

Figure 3:
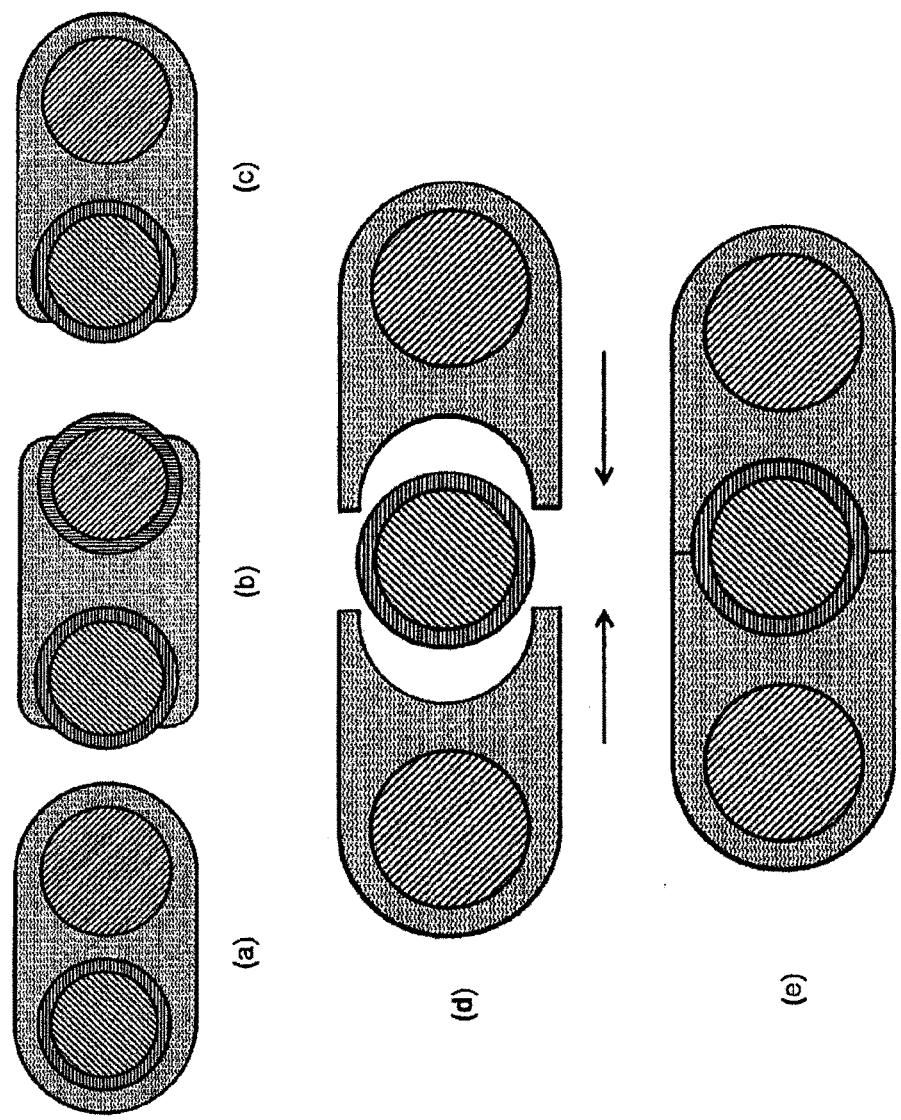

FIG. 3 (a) to (e) show arrangements where an intermediate high thermal conductivity material is used to perform the transfer of thermal energy from the outside of the freeze conduit to the coolant. In general, these configurations should have low thermal resistance similar to the configurations shown in FIGS. 2(h) and (i) and so are more energy efficient. They also have further added benefits in terms of having no direct interface between the outside of the freeze conduit and the coolant allowing the coolant to be at higher pressure than would normally be possible with the relatively weak material of the freeze conduit, as may be required if the coolant fluid is a vapour compression refrigerant such as R404 or R134A.

Figure 4:
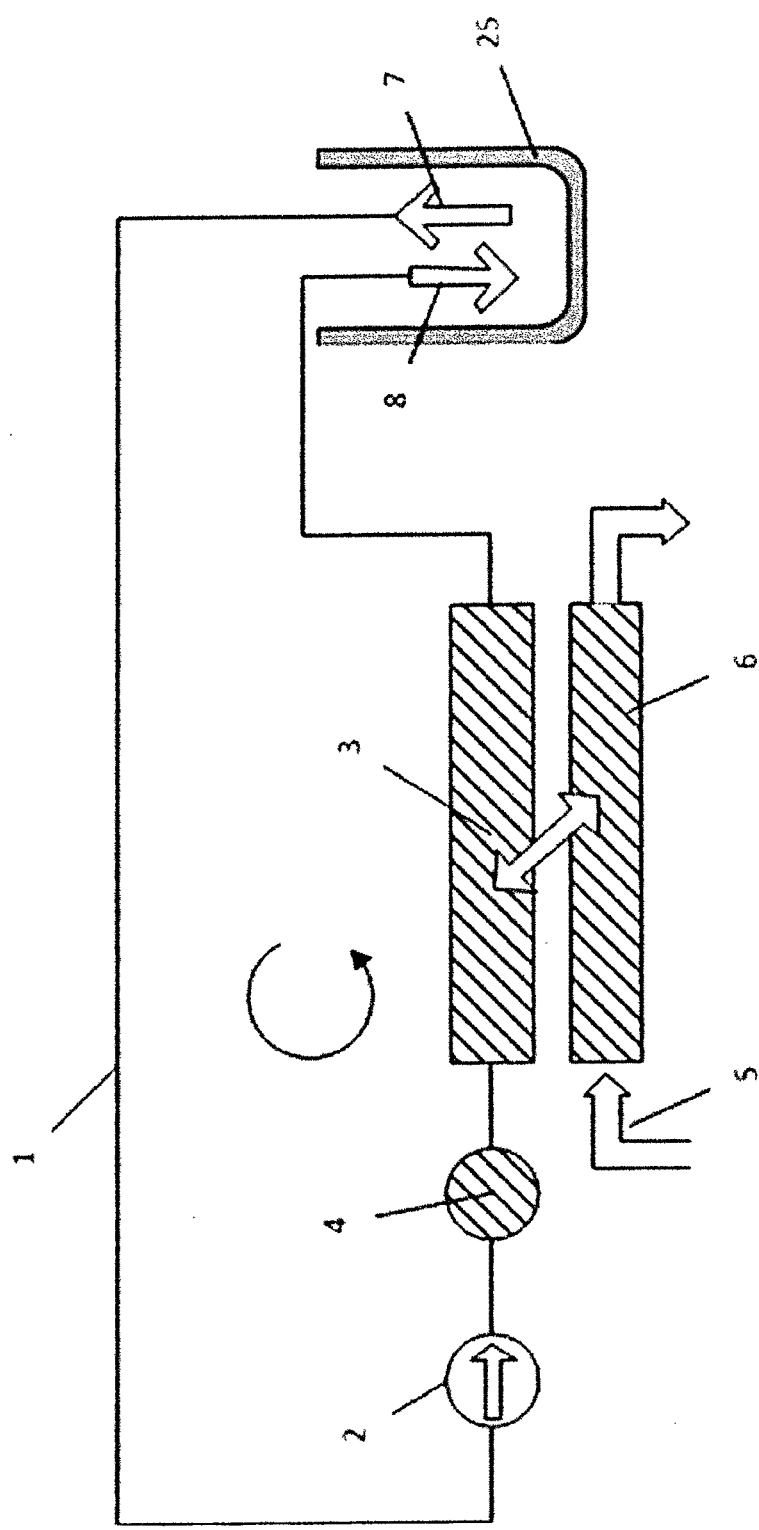
FIG. 4 is a diagrammatic view of a second embodiment of the invention.
Figure 5:
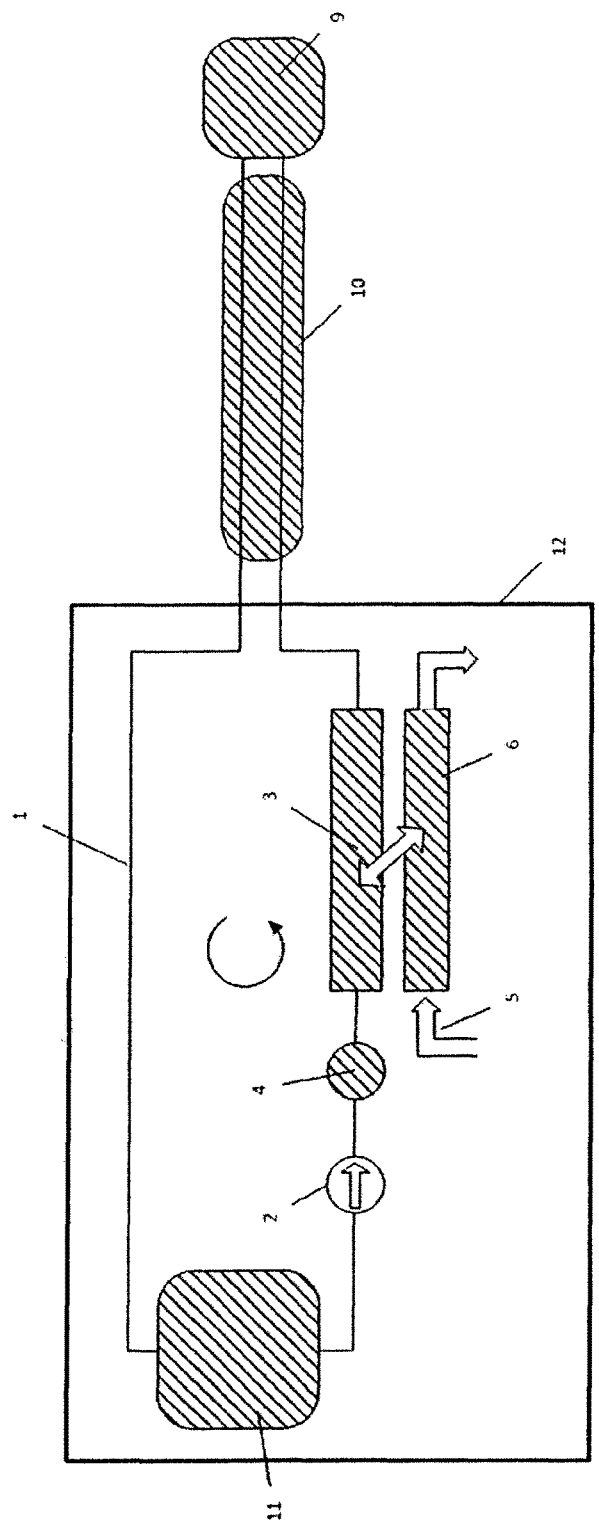
FIG. 5 is a diagrammatic view of a third embodiment of the invention.

FIG. 4 shows an embodiment of the system where the liquid loop 1 includes an open reservoir 25 from which the inlet 7 actively draws the working fluid and into which the dispensing outlet 8 continuously dispenses. Such a system may be used where it is undesirable to have a sealed slush reservoir such as when large quantities of slush must be stored for air conditioning purposes. This system may also be used as a slush beverage device where the main body of beverage is contained within an open reservoir such as a jug; the beverage may be drawn from the jug, turned into a slush and then returned to the jug FIG. 5 shows an embodiment of the system suitable for cryotherapy use with the addition of a cooling 'cuff' 9 suitable to apply cooling to an injured body part, flexible insulated slush recirculation umbilical 10 and a working fluid reservoir 11 for slush storage. This system is beneficial as the combination of the thermal resistance of the cuff and the freeze point of the working fluid allows controlled and consistent application of cryotherapy as required.

Figure 6:
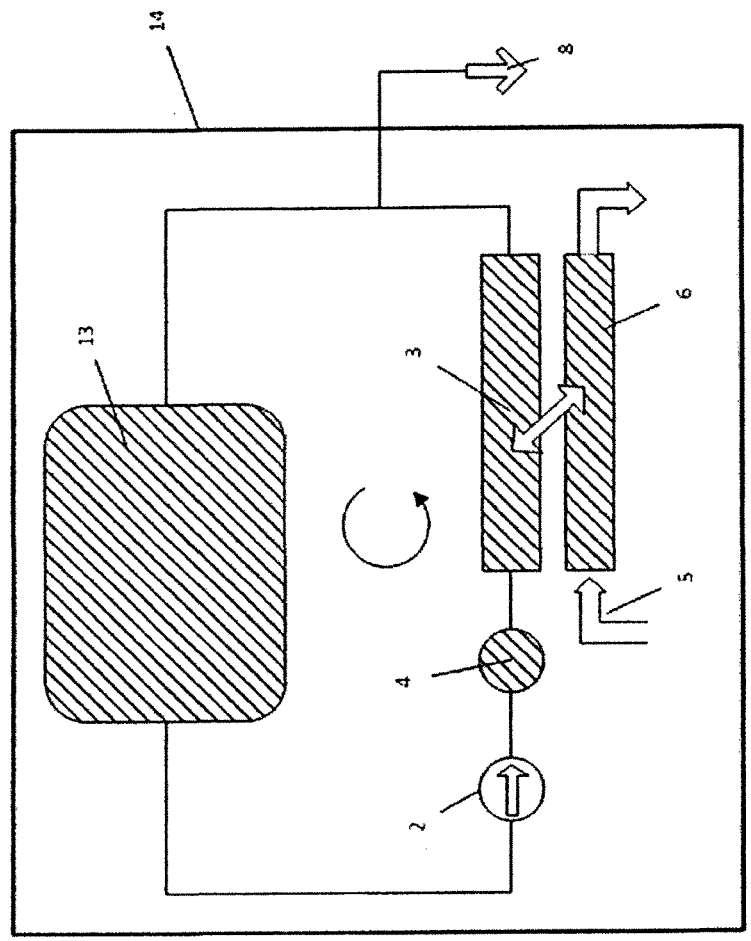
FIG. 6 is a diagrammatic view of a fourth embodiment of the invention.

FIG. 6 shows a system embodiment suitable for use in an application to generate sterile slush for surgical use with the intention of having all disposable wetted parts. The addition of a flexible reservoir 13 within the re-circulated loop 1 allows the system to come pre-charged with working fluid. Pumping of the working fluid can be achieved through the disposable conduit, for example by peristaltic pumping or magnetic drive of a rotor. A dispensing outlet 8 may be provided to allow the sterile slush to be dispensed, or once partially frozen the disposable insert may be removed and cut open to dispense the slush inside. For such a system, the conduit configurations of FIGS. 3 (b) and (c) may be appropriate: the freeze conduit is not fully enclosed, allowing easy assembly and separation of the (disposable) freeze conduit from the cooling conduit. FIGS. 3(d) and (e) show a similar separable arrangement utilising a split intermediate conductive material to maximise contact area and reduce thermal resistance between the coolant and the working fluid.

Figure 7:
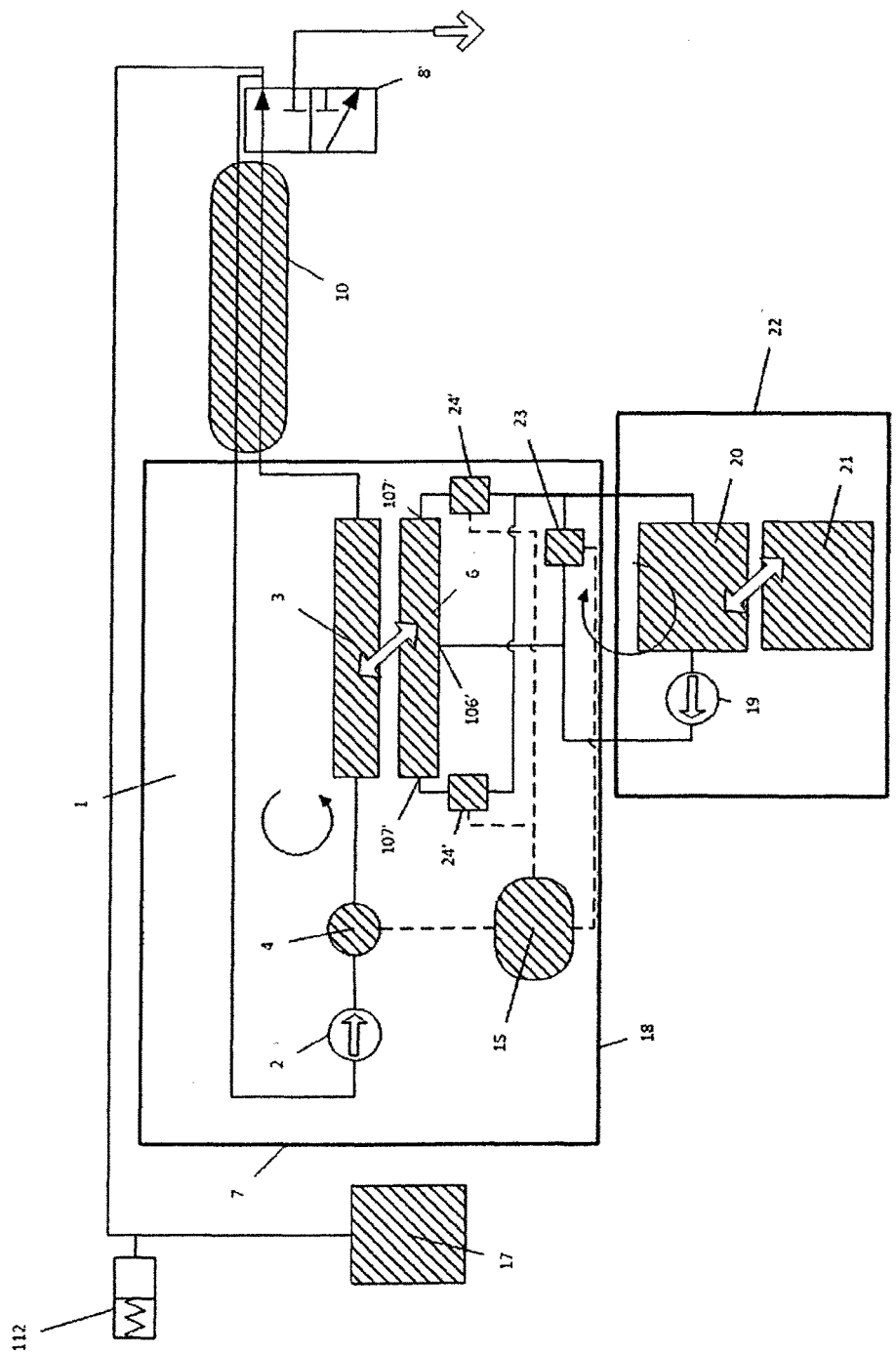
FIG. 7 is a diagrammatic view of a fifth embodiment of the invention.

FIG. 7 shows a system embodiment that has 3 improvements over the system drawn in FIG. 1 while being otherwise substantially similar. The improvements are independent and each may be used without the other as required.

The first improvement is the use of multiple parallel cooling conduit paths within the heat exchanger, acting in this example on a single freeze conduit. As drawn there are two parallel coolant paths but more can be included as required. In the embodiment shown, the coolant is supplied to a central inlet port 106 and leaves the cooling conduit paths from two outlets 107. It can be seen that this arrangement could be reversed with 2 inlets and one central outlet or, if more paths are required, alternating inlet and outlet ports along the length of the cooling conduit. Breaking the cooling conduit into multiple parallel paths achieves many benefits. Firstly the flow restriction is reduced, enabling a higher flow rate for a given pump, resulting in higher cooling power and quicker response. Secondly, given the preferred embodiment of the heat exchanger being the concentric arrangement of cooling conduit around freeze conduit, breaking the cooling conduit into shorter lengths connected by inlet or outlet ports makes assembly of the heat exchanger significantly easier. The separate parallel paths also provide a natural place to install the parallel 2/2 coolant control valves mentioned previously and drawn as 24 in FIG. 7.

The second improvement in the system shown in FIG. 7 is the improved cleanability provided by the 3/2 valve at the dispense tap. The arrangement connects the loop to recirculate when the tap is closed, and diverts the flow to the dispense spout when the tap is open. The input line from the reservoir 17 is directed into the port of the 3/2 valve as drawn such that the recirculation loop becomes a single flow line, with no dead legs, from reservoir to spout when the tap is open. This is important to both be able to achieve effective cleaning of the system and be able to prime the system with working fluid whilst minimising waste occurring due to mixing or dilution. The 3/2 valve arrangement with double port for the input line from the reservoir shown can be implemented as a separate cleaning valve distinct from the dispense tap if required, but the system with the combined cleaning valve and dispense tap as drawn has benefits of reduced component count as well as, for the slush beverage application, the advantage of being cleaned the same way as a standard beer line, making it more familiar for bar staff.

The third improvement is that this embodiment has been provided with an expansion damper 112 to prevent excessive pressure increase due to ice expansion on freezing. At low ice fractions the elasticity of the pipework allows for the modest expansion on freezing. At higher ice fractions, however, the inventors have witnessed the system pressure exceed 10 bar, which may cause standard pipework, connectors and fittings to leak or fail. More elasticity is required, this can be provided using a standard sprung damper normally used to remove pulses on beverage lines that are pumped, and such components generally comprise a piston or diaphragm acting against either a spring or pneumatic pressure. The damper allows a larger change in system volume from expansion with only a small increase in system pressure. As soon as dispense occurs the spring acts to recover the expansion volume, allowing the volume to grow again on freezing after the dispense has finished.

It should be understood that this invention has been described by way of examples only and that a wide variety of modifications can be made without departing from the scope of the invention. In particular, whilst the invention has primarily been described by way of example of a slush beverage dispensing device, it will be appreciated that it may be applicable to other types of comestible as well as non-comestibles and to liquids that are non-aqueous as well as aqueous.

The invention claimed is:

1. An apparatus for generating, at a target ice/liquid ratio with a corresponding target temperature, a slush comprising a frozen and non-frozen liquid, the apparatus comprising:
   a flow path that recirculates the frozen and non-frozen liquid therethrough; and
   a heat exchanger, forming part of the flow path, comprising a coolant conduit extending longitudinally through the heat exchanger and a freeze conduit extending longitudinally through the heat exchanger, wherein the coolant conduit and the freeze conduit share a contiguous boundary along their longitudinal length through the heat exchanger such that thermal energy is transferred between the freeze conduit and the coolant conduit to partially freeze the non-frozen liquid in the conduit loop to generate the slush at the target ice/liquid ratio;
   wherein the freeze conduit is devoid of an ice scraper and the coolant conduit is configured for flow therethrough of coolant at a temperature below the target temperature, the apparatus being configured to vary the rate of coolant flow through the coolant conduit between a first rate and a second rate that is lower than the first rate.

2. The apparatus according to claim 1, configured such that the first rate of coolant flow produces a net increase in a fraction of frozen liquid in the generated slush contained in the freeze conduit.

3. The apparatus according to claim 1, configured such that the second rate of coolant flow produces a net decrease or substantially no change in a fraction of frozen liquid in the generated slush contained in the freeze conduit.

4. The apparatus according to claim 1, configured such that a flow rate of liquid comprising the slush through the freeze conduit is maintained at least 1 liter per minute until ice has nucleated.

5. The apparatus according to claim 1, wherein the coolant comprises a liquid.

6. The apparatus according to claim 1, wherein the coolant comprises a vapor compression refrigerant.

7. The apparatus according to claim 1, wherein the freeze conduit has an maximum internal dimension transverse to the direction of liquid flow that is less than or equal to about 10 mm.

8. The apparatus according to claim 1, wherein the freeze conduit has a length in a range of from 5 m to 30 m.

9. The apparatus according to claim 1, comprising at least one sensor for sensing a fraction of frozen liquid in the generated slush, the apparatus being configured to vary the rate of coolant flow in dependence on an output signal from the at least one sensor.

10. The apparatus according to claim 1, comprising at least one flow restrictor or diverter for restricting or diverting coolant flow through the heat exchanger.

11. The apparatus according to claim 1, comprising a further flow path configured to re-circulate coolant through the coolant conduit.

12. The apparatus according to claim 1, wherein the freeze conduit consists of tubing having a medium density polyethylene (MDPE) or nylon bore.

13. The apparatus according to claim 1, wherein the a coolant conduit is releasably attached to the freeze conduit.

14. The apparatus according to claim 1, wherein the coolant conduit is arranged substantially concentrically with at least a portion of the freeze conduit.

15. The apparatus according to claim 1, wherein the freeze conduit is located within at least a portion of the coolant conduit.

16. The apparatus according to claim 1, wherein the coolant conduit accommodates a maximum coolant volume of 5 liters.

17. The apparatus according to claim 1, wherein the freeze conduit has flexible walls.

18. The apparatus according to claim 1, wherein the liquid is pressurized to above ambient pressure.

19. The apparatus according to claim 1, wherein the target temperature of the slush lies in a range of from less than or equal to about −1° C. to greater than or equal to about −5° C.

20. The apparatus according to claim 1, wherein the coolant temperature is at least about 2° C. lower than the target temperature of the slush.

21. The apparatus according to claim 1, wherein the coolant temperature is less than or equal to about −7° C.

22. The apparatus according to claim 1, wherein the coolant conduit and the freeze conduit are arranged in parallel through the heat exchanger.

23. A method of generating, at a target ice/liquid ratio with a corresponding target temperature, a slush comprising a frozen and non-frozen liquid, the method comprising the steps of:
   providing a flow path that recirculates the frozen and non-frozen liquid therethrough, and a heat exchanger, forming part of the flow path, comprising a coolant conduit extending longitudinally through the heat exchanger and a freeze conduit extending longitudinally through the heat exchanger, wherein the coolant conduit and the freeze conduit share a contiguous boundary along their longitudinal length through the heat exchanger such that thermal energy is transferred between the freeze conduit and the coolant conduit to partially freeze the non-frozen liquid in the freeze conduit to generate the slush at the target ice/liquid ratio, the freeze conduit being devoid of an ice scraper;
   recirculating the frozen and non-frozen liquid through the flow path;
   feeding coolant through the coolant conduit of the heat exchanger at a temperature below the target temperature; and
   varying the rate of coolant flow through the coolant conduit of the heat exchanger between a first rate and a second rate that is lower than the first rate to partially freeze the non-frozen liquid in the freeze conduit to generate the slush at the target ice/liquid ratio.

* * * * *